United States Patent
Hilmisson

(10) Patent No.: US 12,257,067 B2
(45) Date of Patent: Mar. 25, 2025

(54) SYSTEMS AND METHODS FOR DESIGNATION OF REM AND WAKE STATES

(71) Applicant: MyCardio LLC, Denver, CO (US)

(72) Inventor: Hugi Hilmisson, Denver, CO (US)

(73) Assignee: MYCARDIO LLC, Denver, CO (US)

( * ) Notice: Subject to any disclaimer, the term of this patent is extended or adjusted under 35 U.S.C. 154(b) by 0 days.

(21) Appl. No.: 17/762,149

(22) PCT Filed: Sep. 21, 2020

(86) PCT No.: PCT/US2020/051799
§ 371 (c)(1),
(2) Date: Mar. 21, 2022

(87) PCT Pub. No.: WO2021/055943
PCT Pub. Date: Mar. 25, 2021

(65) Prior Publication Data
US 2022/0386946 A1  Dec. 8, 2022

Related U.S. Application Data

(60) Provisional application No. 62/903,833, filed on Sep. 21, 2019.

(51) Int. Cl.
*A61B 5/00* (2006.01)
*A61B 5/0205* (2006.01)
*G16H 10/60* (2018.01)

(52) U.S. Cl.
CPC .......... *A61B 5/4812* (2013.01); *A61B 5/0205* (2013.01); *A61B 5/7278* (2013.01); *A61B 5/7289* (2013.01); *G16H 10/60* (2018.01)

(58) Field of Classification Search
None
See application file for complete search history.

(56) References Cited

U.S. PATENT DOCUMENTS 5,588,425 A  * 12/1996  Sackner ............... A61B 5/0809
                                                       600/513
11,134,887 B2 * 10/2021  Pituch ................... A61B 5/291
(Continued)

FOREIGN PATENT DOCUMENTS

JP    2008-544772 A    12/2008
JP    2009-501060 A    1/2009
(Continued)

OTHER PUBLICATIONS

Thomas et al., Cardiopulmonary coupling spectrogram as an ambulatory clinical biomarker of sleep stability and quality in health, sleep apnea, and insomnia, SLEEPJ, 2018 (Year: 2018).*

(Continued)

*Primary Examiner* — Carl H Layno
*Assistant Examiner* — Manolis Pahakis
(74) *Attorney, Agent, or Firm* — Carter, DeLuca & Farrell LLP

(57) ABSTRACT

The present disclosure provides systems and method of analyzing whether a sleep epoch is a REM sleep epoch or a wake epoch. In accordance with aspects of the present disclosure, a computer-implemented method includes accessing cardiopulmonary coupling data spanning a sleep period for a person, identifying an epoch in the sleep period corresponding to very-low frequency coupling in the cardiopulmonary coupling data, accessing high-frequency coupling data and/or low-frequency coupling data in the cardiopulmonary coupling data corresponding to the epoch, and designating the epoch as a REM sleep epoch or as a wake epoch based on the high-frequency coupling data and/or the low-frequency coupling data corresponding to the epoch, where the epoch is designated based on the cardiopulmonary coupling data without using non-cardiopulmonary coupling physiological data.

12 Claims, 10 Drawing Sheets

(56) References Cited

U.S. PATENT DOCUMENTS

| | | | | |
|---|---|---|---|---|
| 2004/0225179 | A1* | 11/2004 | Kaplan | A61B 5/4809 600/26 |
| 2005/0076908 | A1* | 4/2005 | Lee | A61N 1/3614 600/544 |
| 2005/0115561 | A1* | 6/2005 | Stahmann | G16H 20/40 128/204.23 |
| 2005/0256418 | A1* | 11/2005 | Mietus | A61B 5/4818 600/512 |
| 2005/0267362 | A1* | 12/2005 | Mietus | A61B 5/0816 600/483 |
| 2007/0032733 | A1* | 2/2007 | Burton | A61B 5/7264 600/509 |
| 2010/0049008 | A1* | 2/2010 | Doherty | A61B 5/4812 128/204.23 |
| 2010/0069762 | A1* | 3/2010 | Mietus | A61B 5/0205 600/484 |
| 2010/0240982 | A1* | 9/2010 | Westbrook | A61B 5/4818 600/538 |
| 2010/0249628 | A1* | 9/2010 | Kortelainen | A61B 5/1102 600/527 |
| 2011/0034811 | A1* | 2/2011 | Naujokat | A61B 5/113 600/484 |
| 2012/0016218 | A1 | 1/2012 | Lau et al. | |
| 2012/0179061 | A1* | 7/2012 | Ramanan | A61B 5/4809 128/204.23 |
| 2012/0238800 | A1* | 9/2012 | Naujokat | A61B 5/318 600/26 |
| 2017/0011210 | A1* | 1/2017 | Cheong | A61B 5/681 |
| 2017/0055898 | A1* | 3/2017 | Bandyopadhyay | A61B 5/303 |
| 2017/0347948 | A1* | 12/2017 | Thein | A61B 5/02405 |
| 2017/0360308 | A1* | 12/2017 | Fonseca | A61B 5/4812 |
| 2017/0360363 | A1* | 12/2017 | Fonseca | A61B 5/4806 |
| 2018/0333558 | A1* | 11/2018 | Levendowski | A61B 5/4076 |
| 2019/0166030 | A1* | 5/2019 | Chen | H04L 7/042 |
| 2021/0259561 | A1* | 8/2021 | Hilmisson | A61B 5/7275 |
| 2022/0039742 | A1* | 2/2022 | Hilmisson | A61B 5/4818 |
| 2022/0071511 | A1* | 3/2022 | King | A61B 5/0816 |
| 2023/0021851 | A1* | 1/2023 | Li | A61B 5/0532 |

FOREIGN PATENT DOCUMENTS

| | | | | |
|---|---|---|---|---|
| JP | 2011-526511 | A | 10/2011 | |
| JP | 2012-523935 | A | 10/2012 | |
| WO | WO-2019246234 | A1 * | 12/2019 | A61B 5/0205 |

OTHER PUBLICATIONS

Fonseca et al., Estimating actigraphy from motion artifacts in ECG and respiratory effort signals, 2016 Physiol. Meas. 37 67 (Year: 2016).*

Canadian Office Action for Canadian Application No. 3,155,017 dated Apr. 4, 2023 (3 pages).

Extended European Search Report for Application No. 20864809.7 dated Sep. 6, 2023 (9 pages).

International Search Report and Written Opinion of the International Searching Authority issued in corresponding application PCT/US2020/051799 mailed Dec. 15, 2020 (9 pages).

Notification of Transmittal of International Preliminary Report on Patentability (Chapter II of the Patent Cooperation Treaty) issued in corresponding application PCT/US2020/051799 mailed Sep. 28, 2021 (16 pages).

Office Action issued by the Canadian Intellectual Property Office on Nov. 27, 2023 in corresponding CA Patent Application No. 3155017, pp. 1-4.

Notice of Reasons for Refusal issued by the Japanese Patent Office on Jul. 9, 2024 in corresponding JP Patent Application No. 2022-517752, with English translation.

Examination Report issued in corresponding AU Patent Application No. 2020348479, dated Feb. 6, 2025, pp. 1-4.

* cited by examiner

SYSTEMS AND METHODS FOR DESIGNATION OF REM AND WAKE STATES

CROSS-REFERENCE TO RELATED APPLICATIONS

The present application is a National Stage of, and claims priority to and the benefit of, International Patent Application No. PCT/US2020/051799, filed Sep. 21, 2020, which, in turn, claims the benefit of and priority to U.S. Provisional Application No. 62/903,833, filed Sep. 21, 2019. The contents of each of the foregoing applications are hereby incorporated herein by reference in its entirety.

BACKGROUND

Technical Field

The present disclosure relates to sleep analysis, and in particular, to analysis of cardiopulmonary coupling (CPC) data or CPC data with physiological data during a person's sleep period to designate REM and WAKE states during the sleep period.

Description of Related Art

Cardiopulmonary coupling is a technology for assessing sleep quality by performing a quantitative analysis between two physiological signals—an N-N interval series from heart rate variability coupled with corresponding direct or derived respiration signals—to determine the coherent cross-power of these two signals. Cardiopulmonary coupling is described in, among others, U.S. Pat. Nos. 7,324,845, 7,734,334, 8,403,848, and 8,401,626, which are all hereby incorporated by reference herein in their entirety.

Cardiopulmonary coupling can be characterized in terms of coupling frequency. High frequency coupling represents stable sleep which is a biomarker of integrated stable NREM sleep and is associated with periods of stable breathing, high vagal tone, generally a non-cyclic alternating pattern on the electroencephalogram (EEG), high relative delta power, physiologic blood pressure dipping (in health), and/or stable arousal threshold. In high frequency coupling (HFC), the frequency of coupling is greater than 0.1 Hz.

Low frequency coupling represents unstable sleep, which is a biomarker of integrated unstable NREM sleep, with opposite features to stable sleep. Unstable sleep is associated with EEG activities called cyclic alternating pattern (CAP), periods of fluctuating breathing patterns (tidal volume fluctuations), cyclic variation of heart rate (CVHR), blood pressure non-dipping, and/or variable arousal thresholds. Fragmented REM sleep has low-frequency coupling characteristics. In low frequency coupling (LFC), the frequency of coupling is in range [0.01, 0.1] Hz, inclusive. Low frequency coupling can be further classified as elevated low frequency coupling broad band or elevated low frequency coupling narrow band.

Very low frequency coupling represents REM sleep and WAKE states. The frequency range below 0.01 Hz is defined as Very Low Frequency Coupling (vLFC). REM and WAKE physiology is closely linked from the standpoint of polysomnography (PSG) with the electrooculography used as the main tool for distinguishing between the two states. REM and WAKE have a very similar appearance in cardiopulmonary coupling (CPC), appearing as very low frequency coupling (vLFC).

There is interest in further developing and improving technologies for sleep analysis to designate various states of sleep based on cardiopulmonary coupling data.

SUMMARY

The present disclosure relates to sleep analysis, and in particular, to analysis of cardiopulmonary coupling (CPC) data or CPC data with physiological data during a person's sleep period to designate REM and WAKE states during the sleep period.

In accordance with aspects of the present disclosure, a computer-implemented method includes accessing cardiopulmonary coupling data spanning a sleep period for a person, identifying an epoch in the sleep period including very-low frequency coupling in the cardiopulmonary coupling data, accessing at least one of high-frequency coupling data or low-frequency coupling data in the cardiopulmonary coupling data corresponding to the epoch, and designating the epoch as a REM sleep epoch or as a wake epoch based on the at least one of the high-frequency coupling data or the low-frequency coupling data corresponding to the epoch, where the epoch is designated based on the cardiopulmonary coupling data without using non-cardiopulmonary coupling physiological data.

In various embodiments of the method, the epoch exhibits low-frequency coupling dominance, and the method further includes comparing a power of the very-low frequency coupling during the epoch to a threshold.

In various embodiments of the method, the threshold is based on at least one of: the person, a condition of the person, or a population that includes the person.

In various embodiments of the method, designating the epoch includes designating the epoch as a REM sleep epoch based on: (i) the low-frequency coupling dominance, and (ii) the power of the very-low frequency coupling during the epoch exceeding the threshold.

In various embodiments of the method, the epoch exhibits very-low frequency coupling dominance.

In various embodiments of the method, the very-low frequency coupling dominance for the epoch is based on dominance in a predefined upper range of a very-low frequency coupling range in the cardiopulmonary coupling data corresponding to the epoch.

In various embodiments of the method, designating the epoch includes designating the epoch as a REM sleep epoch based on: (i) the very-low frequency coupling dominance in the predefined upper range of the very-low frequency coupling range, and (ii) power of at least one of low-frequency coupling or high-frequency coupling, in the at least one of the high-frequency coupling data or the low-frequency coupling data corresponding to the epoch, exceeding a threshold.

In various embodiments of the method, designating the epoch includes designating the epoch as a REM sleep epoch based on: (i) the very-low frequency coupling dominance in the epoch, and (ii) presence of elevated low-frequency coupling narrow band in the low-frequency coupling data corresponding to the epoch.

In accordance with aspects of the present disclosure, a system includes one or more processors and at least one memory storing instructions. The instructions, when executed by the one or more processors, cause the system to access cardiopulmonary coupling data spanning a sleep period for a person, identify an epoch in the sleep period including very-low frequency coupling in the cardiopulmonary coupling data, access at least one of high-frequency coupling data or low-frequency coupling data in the cardiopulmonary coupling data corresponding to the epoch, and designate the epoch as a REM sleep epoch or as a wake epoch based on the at least one of the high-frequency coupling data or the low-frequency coupling data corresponding to the epoch, where the epoch is designated based on the cardiopulmonary coupling data without using non-cardiopulmonary coupling physiological data.

In various embodiments of the system, the epoch exhibits low-frequency coupling dominance, and the instructions, when executed by the one or more processors, cause the system to compare a power of the very-low frequency coupling during the epoch to a threshold.

In various embodiments of the system, the threshold is based on at least one of: the person, a condition of the person, or a population that includes the person.

In various embodiments of the system, in designating the epoch, the instructions, when executed by the one or more processors, cause the system to designate the epoch as a REM sleep epoch based on: (i) the low-frequency coupling dominance, and (ii) the power of the very-low frequency coupling during the epoch exceeding the threshold.

In various embodiments of the system, the epoch exhibits very-low frequency coupling dominance.

In various embodiments of the system, the very-low frequency coupling dominance for the epoch is based on dominance in a predefined upper range of a very-low frequency coupling range in the cardiopulmonary coupling data corresponding to the epoch.

In various embodiments of the system, in designating the epoch, the instructions, when executed by the one or more processors, cause the system to designate the epoch as a REM sleep epoch based on: (i) the very-low frequency coupling dominance in the predefined upper range of the very-low frequency coupling range, and (ii) power of at least one of low-frequency coupling or high-frequency coupling, in the at least one of the high-frequency coupling data or the low-frequency coupling data corresponding to the epoch, exceeding a threshold.

In various embodiments of the system, in designating the epoch, the instructions, when executed by the one or more processors, cause the system to designate the epoch as a REM sleep epoch based on: (i) the very-low frequency coupling dominance in the epoch, and (ii) presence of elevated low-frequency coupling narrow band in the low-frequency coupling data corresponding to the epoch.

In accordance with aspects of the present disclosure, a computer-implemented method includes accessing cardiopulmonary coupling data spanning a sleep period for a person, classifying an epoch in the sleep period as a very-low frequency coupling (vLFC) epoch based on the cardiopulmonary coupling data, accessing actigraphy data for the person corresponding to the vLFC epoch, and designating the vLFC epoch as a REM epoch based on a predetermined percentage of actigraphy measurements, in the actigraphy data corresponding to the vLFC epoch, indicating movement below a movement threshold.

In various embodiments of the method, the predetermined percentage is 95% of the actigraphy measurements in the actigraphy data corresponding to the vLFC epoch, and the movement threshold is 0.01 G/s.

In various embodiments of the method, the method includes varying at least one of the predetermined percentage or the movement threshold, for different actigraphy sensors.

In accordance with aspects of the present disclosure, a system includes one or more processors and at least one memory storing instructions. The instructions, when executed by the one or more processors, cause the system to access cardiopulmonary coupling data spanning a sleep period for a person, classify an epoch in the sleep period as a very-low frequency coupling (vLFC) epoch based on the cardiopulmonary coupling data, access actigraphy data for the person corresponding to the vLFC epoch, and designate the vLFC epoch as a REM epoch based on a predetermined percentage of actigraphy measurements, in the actigraphy data corresponding to the vLFC epoch, indicating movement below a movement threshold.

In various embodiments of the system, the predetermined percentage is 95% of the actigraphy measurements in the actigraphy data corresponding to the vLFC epoch, and the movement threshold is 0.01 G/s.

In various embodiments of the system, the instructions, when executed by the one or more processors, further cause the system to vary at least one of the predetermined percentage or the movement threshold, for different actigraphy sensors.

In accordance with aspects of the present disclosure, a computer-implemented method includes accessing cardiopulmonary coupling data spanning a sleep period for a person, classifying an epoch in the sleep period as a very-low frequency coupling (vLFC) epoch based on the cardiopulmonary coupling data, accessing pseudo-actigraphy data for the person corresponding to the vLFC epoch where the pseudo-actigraphy data is based on physiological measurements of the person and is not based on actigraphy measurements, and designating the vLFC epoch as a REM epoch or as a wake epoch based on the pseudo-actigraphy data corresponding to the vLFC epoch.

In various embodiments of the method, the method includes generating the pseudo-actigraphy data corresponding to the vLFC epoch based on signal quality of the physiological measurements.

In various embodiments of the method, generating the pseudo-actigraphy data includes generating data corresponding to greater motion when the signal quality is lower, and generating data corresponding to lesser motion when the signal quality is higher.

In various embodiments of the method, the physiological measurements include at least one of ECG measurements or plethysmography measurements of the person.

In various embodiments of the method, generating the pseudo-actigraphy data includes: processing the physiological measurements to detect peaks during the vLFC epoch, generating the data corresponding to lesser motion when a count of the detected peaks is below a predetermined threshold and when shapes of the detected peaks match expected peak shapes, and generating the data indicating greater motion when the count of the detected peaks is greater than the predetermined threshold and when the shapes of the detected peaks differ from the expected peak shapes.

In various embodiments of the method, the physiological measurements include oxygen saturation measurements.

In accordance with aspects of the present disclosure, a system includes one or more processors and at least one memory storing instructions. The instructions, when executed by the one or more processors, cause the system to access cardiopulmonary coupling data spanning a sleep period for a person, classify an epoch in the sleep period as a very-low frequency coupling (vLFC) epoch based on the cardiopulmonary coupling data, access pseudo-actigraphy data for the person corresponding to the vLFC epoch where the pseudo-actigraphy data is based on physiological measurements of the person and is not based on actigraphy measurements, and designate the vLFC epoch as a REM epoch or as a wake epoch based on the pseudo-actigraphy data corresponding to the vLFC epoch.

In various embodiments of the system, the instructions, when executed by the one or more processors, cause the system to generate the pseudo-actigraphy data corresponding to the vLFC epoch based on signal quality of the physiological measurements.

In various embodiments of the system, in generating the pseudo-actigraphy data, the instructions, when executed by the one or more processors, cause the system to generate data corresponding to greater motion when the signal quality is lower, and generate data corresponding to lesser motion when the signal quality is higher.

In various embodiments of the system, the physiological measurements include at least one of ECG measurements or plethysmography measurements of the person.

In various embodiments of the system, in generating the pseudo-actigraphy data, the instructions, when executed by the one or more processors, cause the system to: process the physiological measurements to detect peaks during the vLFC epoch, generate the data corresponding to lesser motion when a count of the detected peaks is below a predetermined threshold and when shapes of the detected peaks match expected peak shapes, and generate the data indicating greater motion when the count of the detected peaks is greater than the predetermined threshold and when the shapes of the detected peaks differ from the expected peak shapes.

In various embodiments of the system, the physiological measurements include oxygen saturation measurements.

In accordance with aspects of the present disclosure, a computer-implemented method includes accessing cardiopulmonary coupling data spanning a sleep period for a person, classifying an epoch in the sleep period as a very-low frequency coupling (vLFC) epoch based on the cardiopulmonary coupling data, accessing physiological data for the person corresponding to the vLFC epoch where the physiological data includes physiological measurements and does not include actigraphy measurements, and designating the vLFC epoch as a REM epoch based on the physiological data corresponding to the vLFC epoch indicating sleep-disordered breathing.

In various embodiments of the method, the physiological measurements include oxygen saturation measurements, and the method includes processing the oxygen saturation measurements to identify sleep-disordered breathing events during the vLFC epoch.

In accordance with aspects of the present disclosure, a system includes one or more processors and at least one memory storing instructions. The instructions, when executed by the one or more processors, cause the system to access cardiopulmonary coupling data spanning a sleep period for a person, classify an epoch in the sleep period as a very-low frequency coupling (vLFC) epoch based on the cardiopulmonary coupling data, access physiological data for the person corresponding to the vLFC epoch where the physiological data includes physiological measurements and does not include actigraphy measurements, and designate the vLFC epoch as a REM epoch based on the physiological data corresponding to the vLFC epoch indicating sleep-disordered breathing.

In various embodiments of the system, the physiological measurements include oxygen saturation measurements, and the instructions, when executed by the one or more processors, cause the system to process the oxygen saturation measurements to identify sleep-disordered breathing events during the vLFC epoch.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

The present disclosure relates to analysis of cardiopulmonary coupling (CPC) data or CPC data with physiological data during a person's sleep period to designate REM and WAKE states during the sleep period. During REM sleep, a subject remains near motionless or in a state of "skeletal muscular paralysis," where the primary mechanical motion is in the eyes. Because REM presents as vLFC and should be absent of any significant motion, one approach according to the present disclosure identifies REM state based on vLFC without sufficient actigraphy and identifies WAKE state based on vLFC with sufficient actigraphy. Other aspects of the present disclosure do not use actigraphy data to designate REM or WAKE states. For example, pseudo-actigraphy data can be used, as described in more detail later herein. Other aspects of the present disclosure use only cardiopulmonary coupling data to designate REM or WAKE states, without using any non-CPC physiological data, which will be described later herein.

Figure 1:
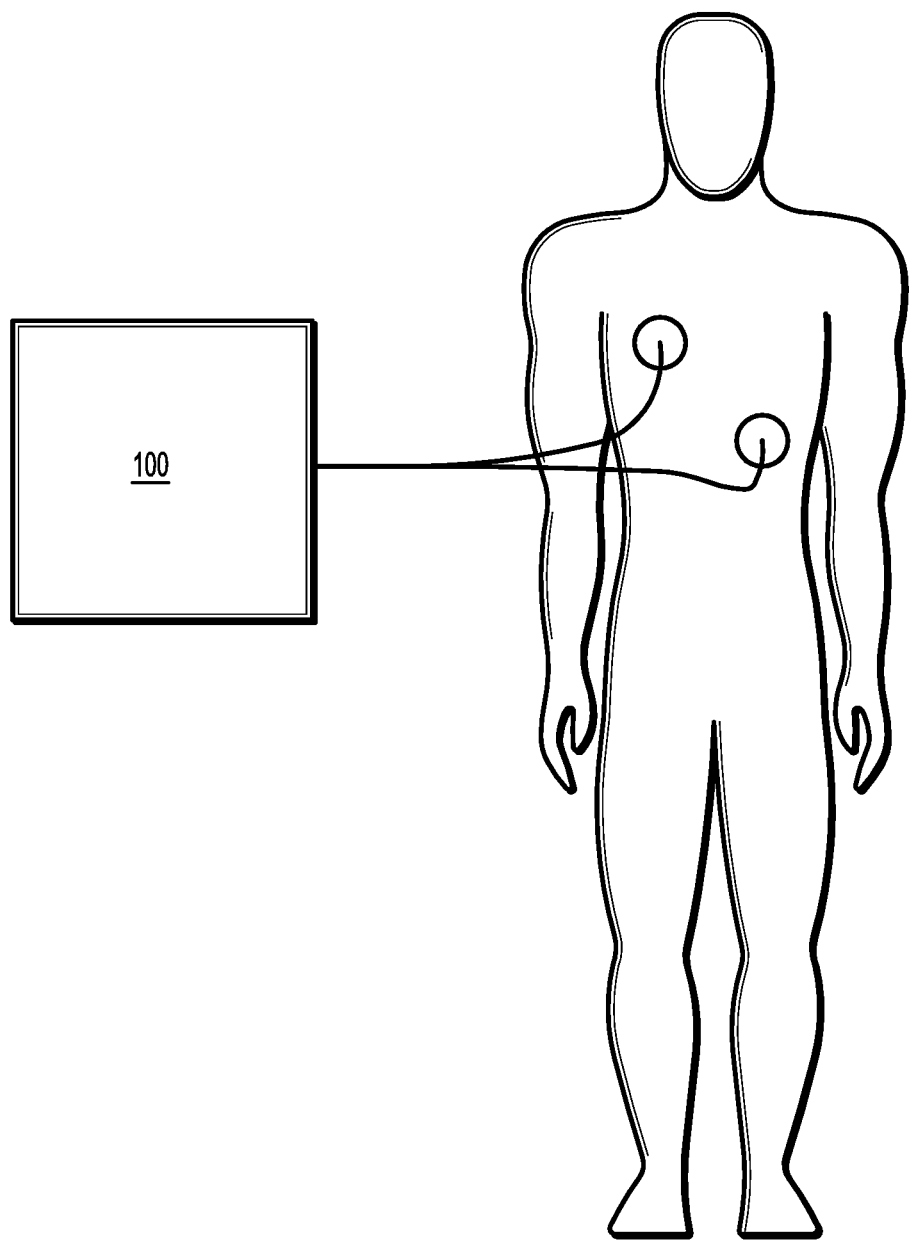
FIG. 1 is an illustration of an exemplary measurement system, in accordance with aspects of the present disclosure.

Referring now to FIG. 1, there is shown an illustration of an exemplary measurement system 100 in accordance with aspects of the present disclosure. The measurement system 100 can be attached to a person during sleep to obtain physiological measurements that can be used to compute cardiopulmonary coupling ("CPC"), such as electrocardiogram measurements or other physiological measurements. The measurement system 100 also obtains various measurements, such as ECG measurements, plethysmography measurements, oxygen saturation measurements, and/or actigraphy measurements, whose use will be described later herein. FIG. 1 is exemplary, and various sensors may be located at different portions of the person's body, including portions not shown in FIG. 1. For example, various sensors may be located at a person's torso, head, and/or limbs, among other locations. The various sensors for detecting the physiological signals will be understood by persons skilled in the art. For example, in various embodiments, the sensors may be sensors which touch the body of a person or may be touch-less sensors that do not directly touch the person (e.g., sensors based on ballistocardiography). The physiological measurements can be recorded in a storage medium, such as a disk drive, flash drive, solid state drive, or other storage medium. In various embodiments, the various physiological measurements can be recorded in parallel. In various embodiments, each recorded data can be tagged or associated with a time stamp. By tagging or associating recorded data with time stamps, various recorded measurements can be correlated in time. It is contemplated that other ways of correlating recorded measurements in time can be employed.

Figure 2:
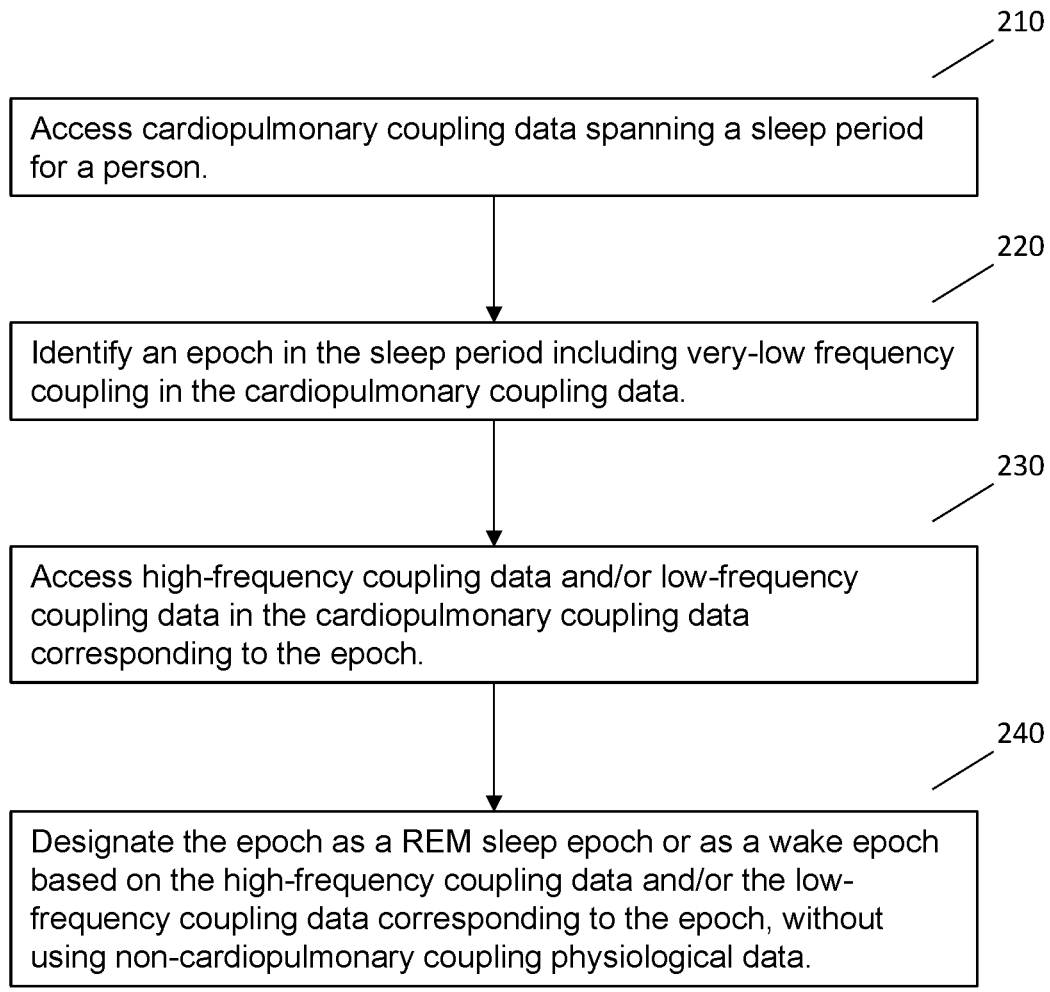
FIG. 2 is a flow diagram of an exemplary operation for designating REM/Wake states based on cardiopulmonary coupling data, in accordance with aspects of the present disclosure.

One aspect of the present disclosure relates to systems and methods for designating REM or WAKE state based on cardiopulmonary coupling spectral analysis without using non-CPC data. As described above, very low frequency coupling (vLFC) represents REM sleep or WAKE states. FIG. 2 shows an exemplary operation of analyzing CPC data from a sleep period of a person to distinguish between REM sleep and WAKE state, without using non-CPC physiological data. In the description herein, a sleep period can be divided into segments which may be referred to herein as "epochs." In various embodiments, different epochs may have the same duration or different epochs may have different durations.

With reference to FIG. 2, at block 210, the operation involves accessing cardiopulmonary coupling data spanning a sleep period for a person. The CPC data can be accessed, for example, from the measurement system of FIG. 1 or from another system. At block 220, the operation involves identifying an epoch in the sleep period including very-low frequency coupling in the cardiopulmonary coupling data. As described in more detail below, the epoch including very-low frequency coupling (vLFC) may have vLFC dominance (i.e., highest frequency coupling power is in the vLFC band) or may not have vLFC dominance. At block 230, the operation involves accessing high-frequency coupling data and/or low-frequency coupling data in the cardiopulmonary coupling data corresponding to the epoch. At block 240, the operation involves designating the epoch as a REM sleep epoch or as a wake epoch based on the high-frequency coupling data and/or the low-frequency coupling data corresponding to the epoch, without using non-cardiopulmonary coupling physiological data. The operation of FIG. 2 can be implemented by a computing system, such as the computing system of FIG. 9, which will be described later herein. The following describes embodiments of the operation of FIG. 2.

The following description relates to epochs which contain vLFC coupling but where the dominant CPC state for the epoch has been classified as low frequency coupling (LFC), i.e., highest frequency coupling power is in the LFC band. During such epochs, vLFC power is non-zero and is less than the LFC power.

Figure 3:
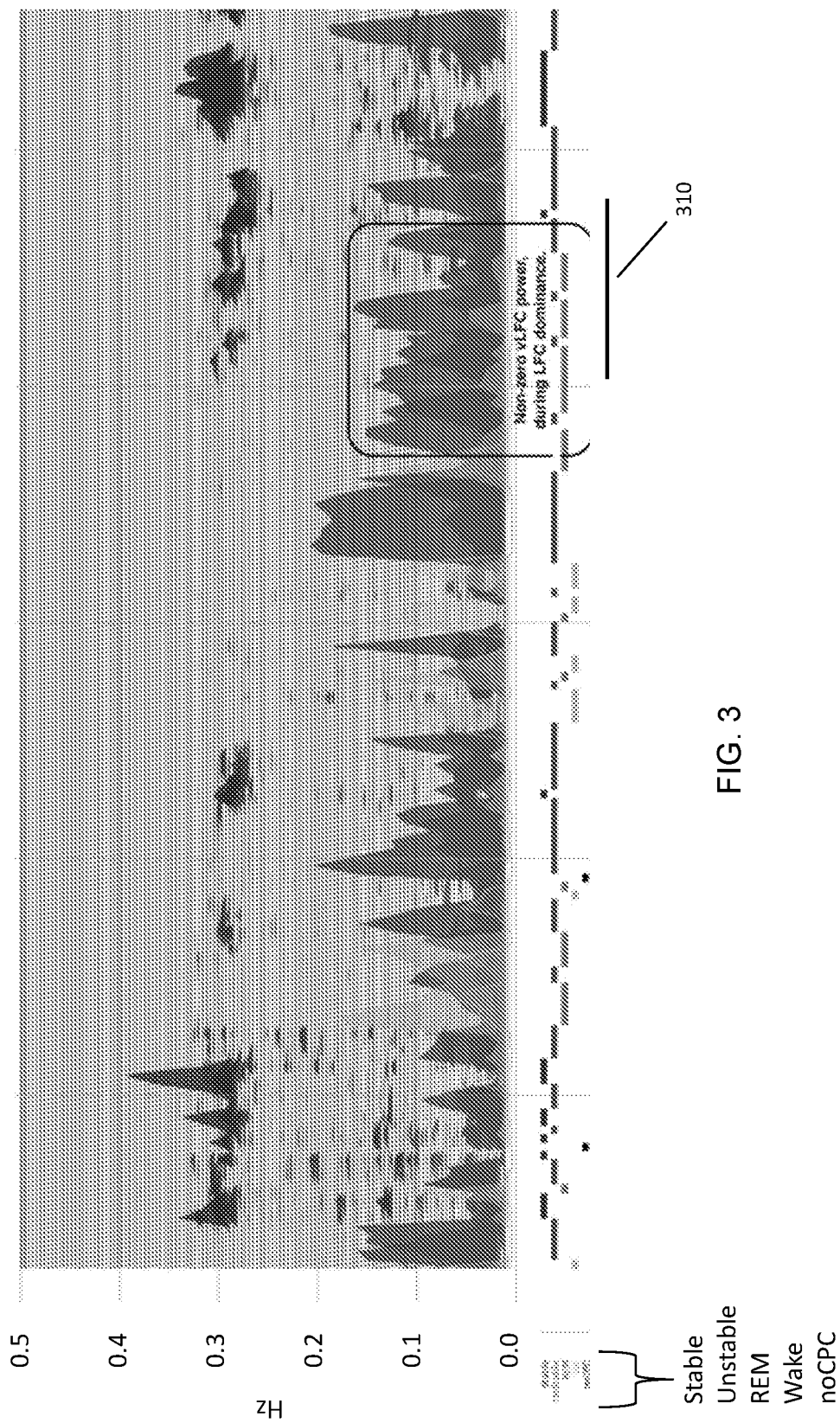
FIG. 3 is a diagram of an exemplary epoch having non-zero vLFC power during LFC dominance, in accordance with aspects of the present disclosure.

In accordance with aspects of the present disclosure, for epochs of non-zero vLFC power and LFC dominance, such epochs can be characterized as fragmented REM as opposed to unstable NREM. During epochs of fragmented REM and in the absence of upper vLFC frequency band dominance, such an epoch can be designated as REM sleep state based on dynamic thresholds applied in the vLFC band, where the dynamic threshold can be different for different persons. An example of such an epoch is shown in FIG. 3, where an epoch 310 is shown with non-zero vLFC power and LFC dominance.

In such epochs with non-zero vLFC power and LFC dominance, REM classification may not be based on fixed thresholds, in view of the designation being based on a non-zero vLFC power as opposed to vLFC dominance. Rather, a dynamic threshold permits the designation of REM sleep and WAKE state to be more accurate. For example, a particular fixed threshold may be suitable for a person with healthy sleep, but that particular threshold may not accurately designate REM sleep and WAKE states for a person with unhealthy sleep whose deteriorating condition could affect the vLFC band. Accordingly, dynamic thresholds suitable for different conditions, persons, or populations, among other things, can be used to designate REM sleep and WAKE in epochs with non-zero vLFC power and LFC dominance (e.g., FIG. 3). In various embodiments, the dynamic threshold can be based on the average of a particular population. For example, if an epoch has LFC dominance and vLFC power is above the average vLFC power of the particular population, then the epoch can be classified as REM. Other types of dynamic thresholds are contemplated to be within the scope of the present disclosure.

The following description relates to epochs where the dominant CPC state has been classified as vLFC. In accordance with aspects of the present disclosure, designating a vLFC epoch as REM state or WAKE state is based on analysis of CPC frequency bands after the dominant CPC state has been classified as vLFC.

Figure 4:
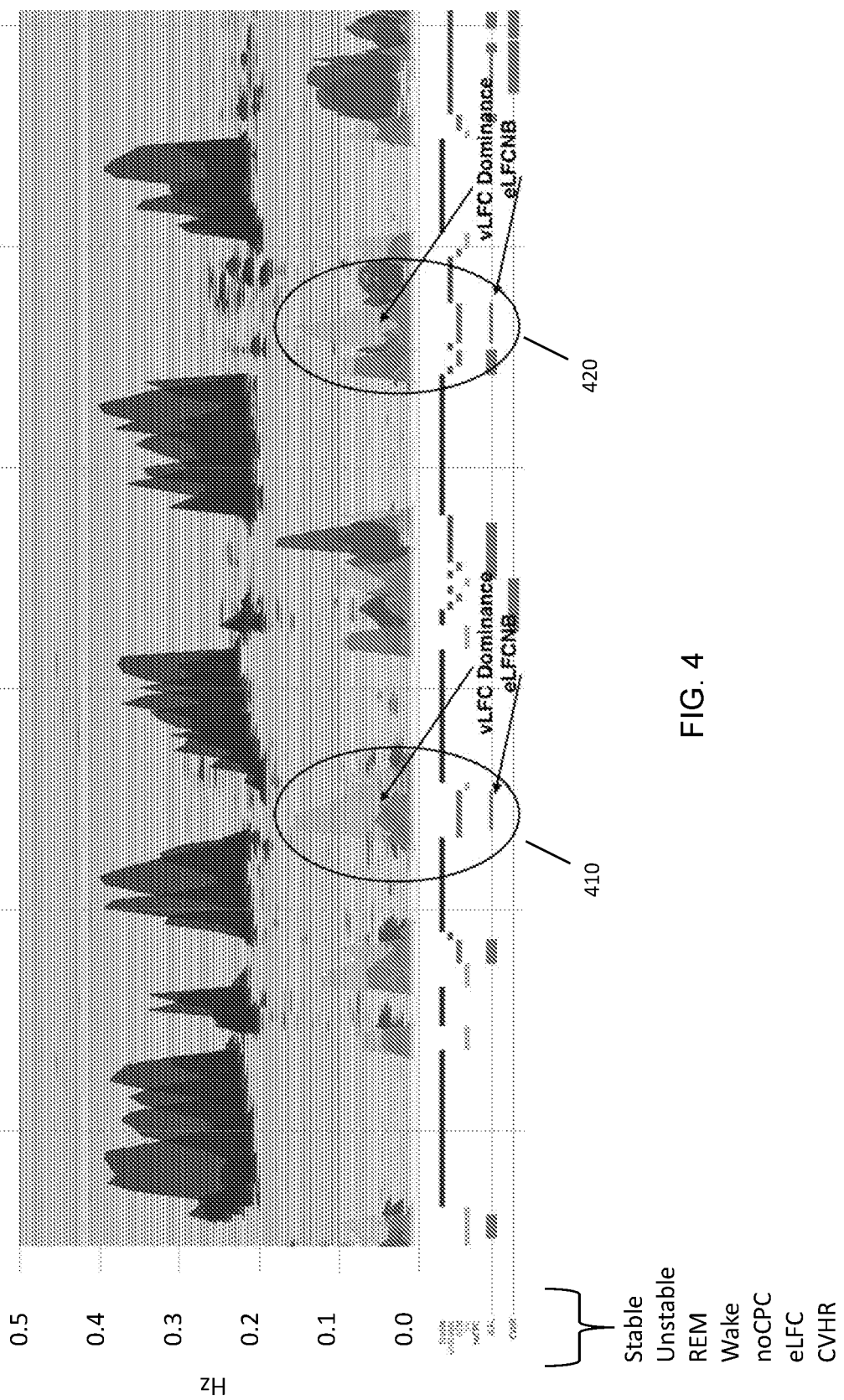
FIG. 4 is a diagram of exemplary epochs having $eLFC_{NB}$ during vLFC dominance, in accordance with aspects of the present disclosure.

In various embodiments, an epoch with vLFC dominance can be designated as REM state when there is activation (e.g., non-zero power) in the LFC band and/or the HFC band and when the dominant CPC frequency is in the upper range of the vLFC band (e.g., close to but not exceeding 0.01 Hz). FIG. 4 shows examples of such epochs 410, 420.

In various embodiments, an epoch with vLFC dominance can be designated as REM state when Elevated Low Frequency Coupling Narrow Band (eLFC$_{NB}$) is also present. Low frequency coupling can be sub-categorized as elevated low frequency coupling broad band (eLFC$_{BB}$) or fragmentation, elevated low frequency coupling narrow band (eLFC$_{NB}$) or periodicity, or no elevated low frequency coupling. eLFC$_{NB}$ is a marker of periodicity and is associated with periodic breathing, Cheyne-Stokes respiration, and central apneas. eLFC$_{BB}$ can be caused by other disorders such as pain or other disturbances during sleep that cause fragmentation, while eLFC$_{NB}$ can be caused by periodic limb movements.

FIG. 4 shows examples of epochs 410, 420 with vLFC dominance where eLFC$_{NB}$ is also present. During testing, such epochs were designated as REM state based on polysomnography data and were also accurately designated based on CPC data alone. As used herein, the term Elevated Very Low Frequency Coupling Narrow Band (eVLFC$_{NB}$), or "Periodic REM" sleep, will be used to identify occurrence of Elevated Low Frequency Coupling Narrow Band (eLFC$_{NB}$) during dominance in the vLFC frequency band. It will be understood that eVLFC$_{NB}$, or Periodic REM, can serve as a new CPC state. Accordingly, an approach to designating REM sleep and WAKE states is configured to designate eVLFC$_{NB}$ as REM sleep state. If eVLFC$_{NB}$ is not present, then as mentioned above, dominance in the upper range of the vLFC band (e.g., CPC frequency power exceeding 0.05 but less than the total power in the vLFC band) can be used to designate the epoch as REM sleep state.

Accordingly, FIGS. 2-4 and the description above show embodiments where an epoch can be designated as REM sleep state by analyzing only CPC data and without using non-CPC data. The embodiments described above and the embodiments of FIGS. 2-4 are exemplary and do not limit the scope of the present disclosure.

Another aspect of the present disclosure relates to systems and methods for designating REM or WAKE state based on analyzing cardiopulmonary data together with various physiological signals, such as actigraphy, oxygen saturation, and/or pseudo-actigraphy physiological signals such as ECG and plethysmography. Use of CPC data together with actigraphy data will be described in connection with FIGS. 5 and 6. Use of CPC data together with pseudo-actigraphy physiological data and/or oxygen saturation data will be described in connection with FIG. 7 and FIG. 10.

Figure 5:
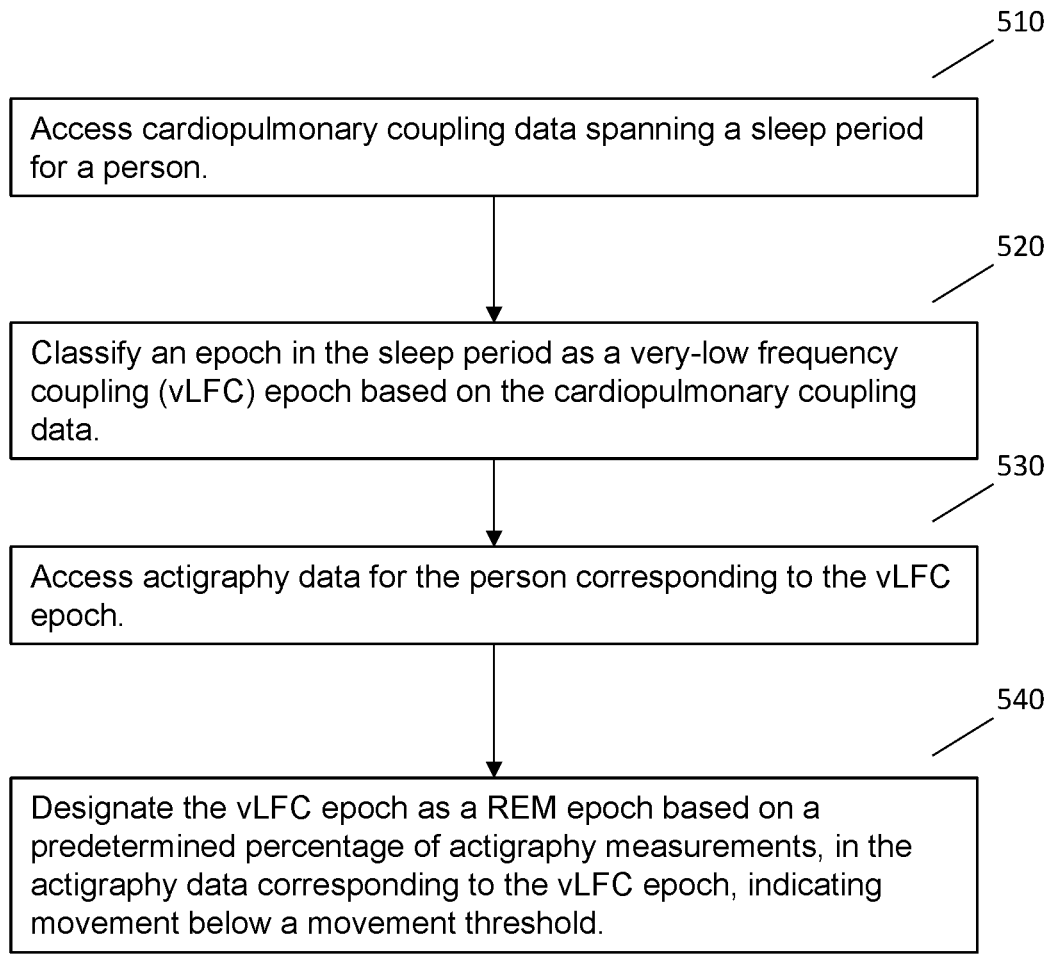
FIG. 5 is a flow diagram of an exemplary operation for designating REM/Wake states based on CPC data together with actigraphy data, in accordance with aspects of the present disclosure.

In accordance with aspects of the present disclosure, FIG. 5 shows a flow diagram of an exemplary operation of designating REM or WAKE state based on analyzing cardiopulmonary data together with actigraphy data. The operation applies a threshold on the measurement of motion to designate an epoch as REM or WAKE states. In various embodiments, in order to collect information on movement, a recording device (e.g., hardware) includes an accelerometer sensor. Accelerometers are sensor devices that measure acceleration (rate of change in velocity) of an object, which for the present disclosure is a person. In accordance with aspects of the present disclosure, a raw actigraphy signal can be processed to generate a quantity that reports acceleration with a certain unit of measurement. Common units of measurement are m/s$^2$ or G-force. Actigraphy data can be obtained and stored using the system of FIG. 1, for example.

With continuing reference to FIG. 5, in block 510, the operation involves accessing cardiopulmonary coupling data spanning a sleep period for a person. In block 520, the operation involves classifying an epoch in the sleep period as a very-low frequency coupling (vLFC) epoch based on the cardiopulmonary coupling data. The classification can be based on vLFC dominance in the epoch. In block 530, the operation involves accessing actigraphy data for the person corresponding to the vLFC epoch. The actigraphy data can be accessed from a storage or computing system, which will be described in connection with FIG. 9. The actigraphy data corresponding to the vLFC epoch can be identified based on time stamps, for example. In block 540, the operation involves designating the vLFC epoch as a REM epoch based on a predetermined percentage of actigraphy measurements, in the actigraphy data corresponding to the vLFC epoch, indicating movement below a movement threshold. An example is provided below.

In various embodiments, for designating REM vs. WAKE states, a threshold value of 0.01 G/s can be used, such that acceleration below 0.01 G/s is treated as indicative of REM sleep, while acceleration at or above 0.01 G/s is treated as indicative of WAKE state. The particular value of the threshold is exemplary and other values can be used. In various embodiments, the number of acceleration samples exceeding the threshold is compared to the total number of samples in the epoch, to produce a measure for designating the epoch as REM sleep state or WAKE state. In various embodiments, if 95% of the acceleration samples in an epoch are below the threshold, then the epoch can be designated as REM state. Otherwise, the epoch would be designated as WAKE state. The percentage threshold is exemplary and can be another value. In various embodiments, the length of the epoch or period to be analyzed can be modified to increase certainty and to derive a measurement of fragmentation or lack thereof.

In various embodiments, the acceleration threshold value may need to be modified based on accelerometer hardware and firmware specifications (e.g., dynamic range, sampling rate, etc.). For example, new accelerometer sensors may need to be analyzed and compared to reference devices to set the acceleration threshold for REM/WAKE designation.

Figure 6:
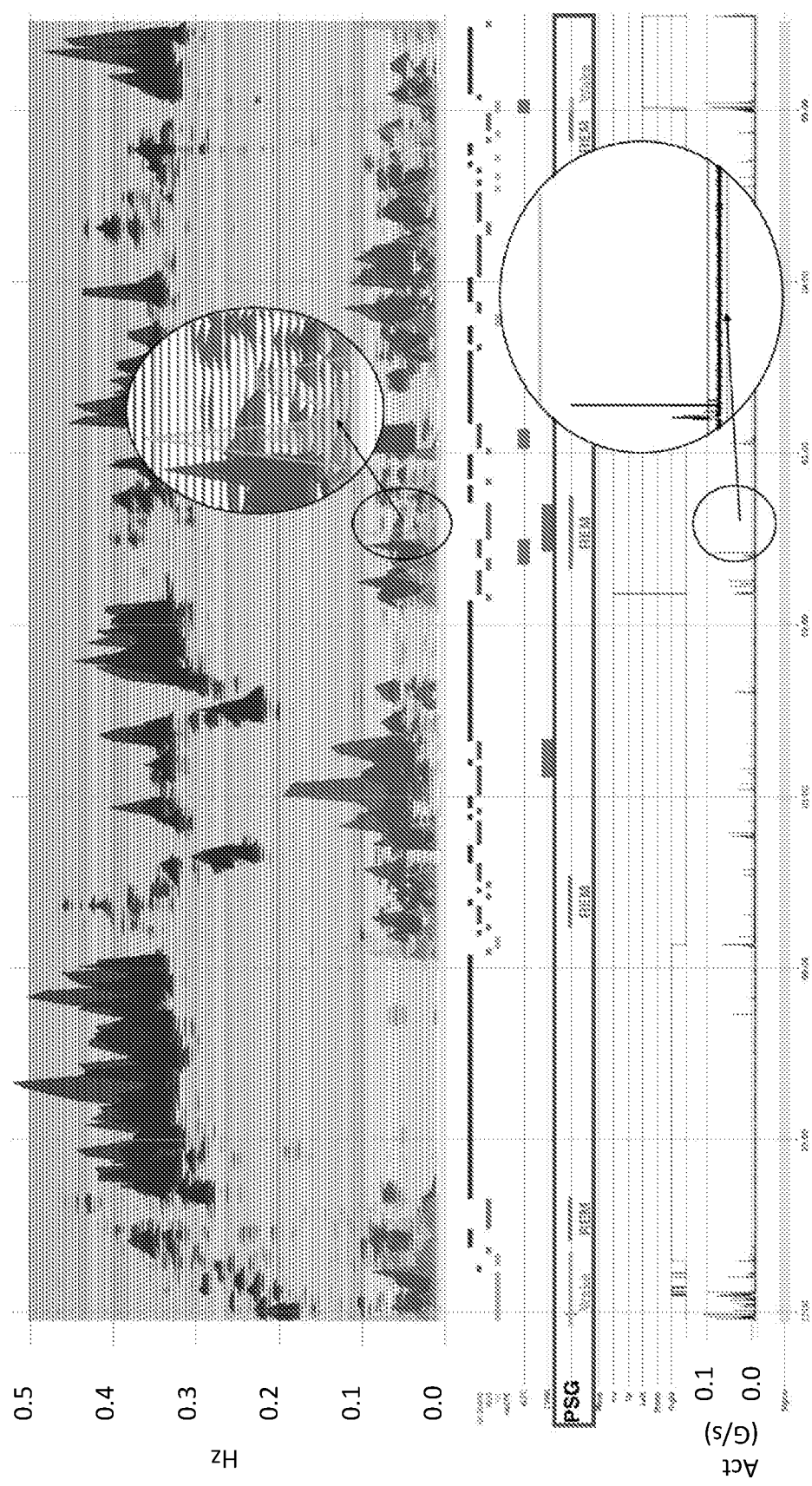
FIG. 6 is a diagram of an exemplary epoch having vLFC dominance and corresponding to actigraphy signals indicating movement, in accordance with aspects of the present disclosure.

FIG. 6 shows an example of CPC and physiological data where REM/WAKE states were designated based on the operation of FIG. 5. For comparison to a PSG reference, extended periods of WAKE and all REM periods, scored by PSG, are shown in the purple box.

Figure 7:
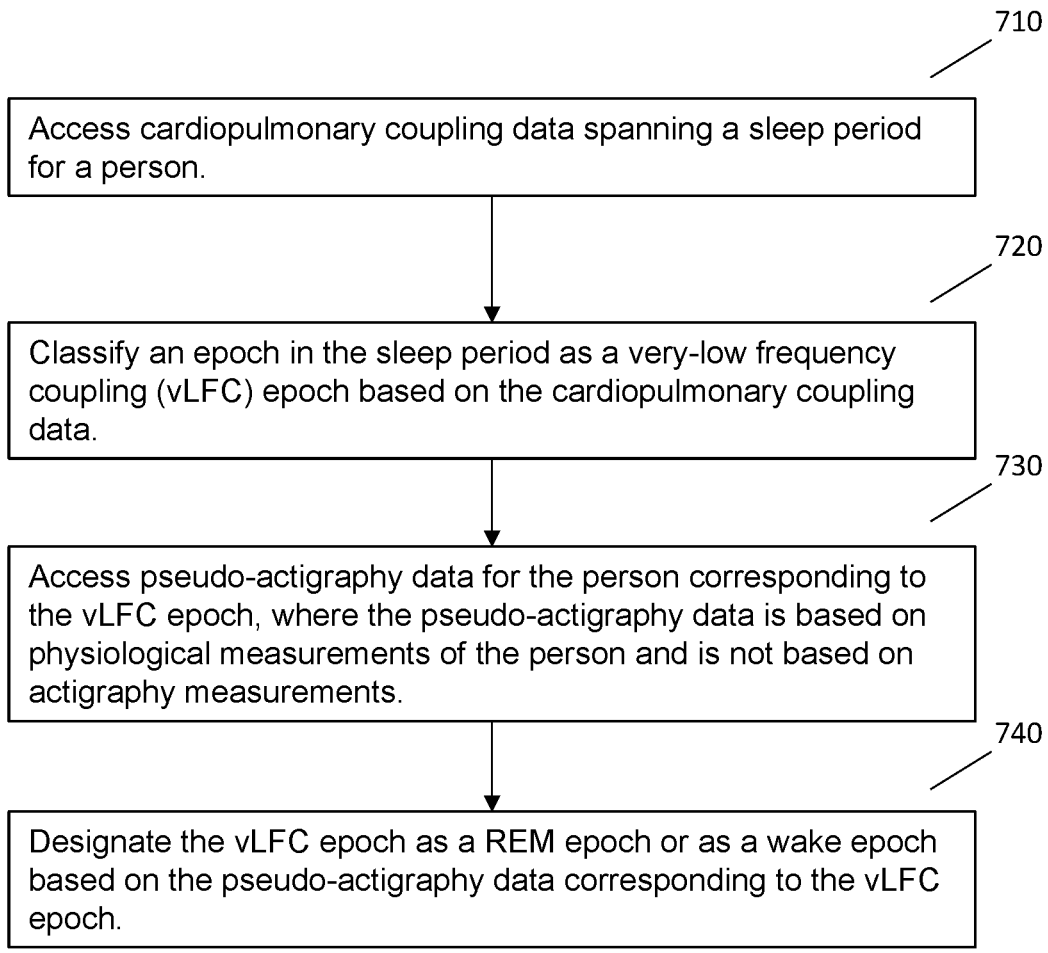
FIG. 7 is a flow diagram of an exemplary operation for designating REM/Wake states based on CPC data together with pseudo-actigraphy data, in accordance with aspects of the present disclosure.

In accordance with aspects of the present disclosure, FIG. 7 shows a flow diagram of an exemplary operation of designating REM or WAKE state based on analyzing cardiopulmonary data together with pseudo-actigraphy data. As used herein, the term "pseudo-actigraphy signal" or data refers to a non-actigraphy physiological signal that has certain characteristics which are indicative of actigraphy. A pseudo-actigraphy signal can include, for example, ECG signals, plethysmography signals, and oxygen saturation signals, among others. In various embodiments, a pseudo-actigraphy signal can be a physiological signal whose signal quality increases when a person is in REM state and decreases when the person is in WAKE state. The signal quality can degrade, for example, by changes affecting signal strength, signal validity, or signal presence, among other things. In accordance with aspects, intermittent deterioration of signal quality correlates with motion artifact and can be utilized as pseudo-actigraphy. In various embodiments, intermittent deterioration of signal quality during vLFC dominance can be designated as WAKE state, while near pristine or pristine signal quality during vLFC dominance can be designated as REM state. Accordingly, the disclosed systems and methods can analyze a pseudo-actigraphy signal to designate an epoch as REM or WAKE states.

With continuing reference to FIG. 7, in block 710, the operation involves accessing cardiopulmonary coupling data spanning a sleep period for a person. In block 720, the operation involves classifying an epoch in the sleep period as a very-low frequency coupling (vLFC) epoch based on the cardiopulmonary coupling data. For example, the vLFC epoch can exhibit vLFC dominance. In block 730, the operation involves accessing pseudo-actigraphy data for the person corresponding to the vLFC epoch. The pseudo-actigraphy data is based on physiological measurements of the person and is not based on actigraphy measurements. As mentioned above, pseudo-actigraphy data can include ECG signals, plethysmography signals, and oxygen saturation signals, among others. In block 740, the operation involves designating the vLFC epoch as a REM epoch or as a wake epoch based on the pseudo-actigraphy data corresponding to the vLFC epoch. The operation of FIG. 7 can be implemented in a computing system, such as the computing system of FIG. 9, which will be described later herein. Various embodiments of the operation of FIG. 7 are described below.

In accordance with aspects of the present disclosure, with respect to ECG and plethysmography signals, the signal quality can be quantified by evaluating the performance of the feature extraction for the ECG and plethysmography signals. For ECG, such features include, but are not limited to, R-peaks, P-waves, ST segments, and/or QRS complexes, among others. For plethysmography, such features include, but are not limited to, systolic peaks, diastolic peaks, and/or dicrotic notches, among others. When the signal deteriorates and/or results in an absence of detected features, the signal quality outcome decreases.

In various embodiments, certain features may be rejected. During periods of weak signal, a detector may be unsuccessful in detecting features of the signal, thereby resulting in "missing features." In various embodiments, every marked feature can be compared to a preset template, and a correlation to the template can be calculated. During periods of motion artifact, the signal will become distorted and the correlation between the marked feature and the template will be low, and the feature may be rejected as a "rejected feature".

In various embodiments, the signal quality can be quantified by comparing the quantity of detected features to an expected number of detected features for a given time segment. The length of the time segment can be varied depending on the desired granularity. In various embodiments, signal quality can be expressed as a percentage of expected features for a chosen time segment which are marked features.

In various embodiments, when the detected features are signal peaks, signal quality can be quantified as data corresponding to lesser motion when a count of detected peaks is below a predetermined threshold and when shapes of the detected peaks match expected peak shapes, and can be quantified as data indicating greater motion when the count of the detected peaks is greater than the predetermined threshold and when the shapes of the detected peaks differ from the expected peak shapes.

In accordance with aspects of the present disclosure, with respect to oxygen saturation signals, the signal quality of oxygen saturation signals is based on evaluating the value and the rate of change. Oxygen saturation reports blood oxygen saturation in the range [0%, 100%]. In cases where the sensor is completely disconnected from a person (due to movement, for example), the oxygen saturation values would be expected to drop to 0%. During these periods, the signal quality would be zero (0). Intermittent disconnect from the subject, such as due to movement, may result in poor sensor contact but not a complete disconnect. In these circumstances, the oxygen saturation values will drop rapidly at a rate implausible for actual human physiology.

In accordance with aspects of the present disclosure, the rate of oxygen saturation drop is evaluated and compared to a threshold value, such as a threshold value of 3% per second change (i.e., 0.03/s), or another value. In various embodiments, during periods where the threshold is violated, the signal quality value can be set to zero (0), and otherwise, the signal quality value can be set to one (1). Other ways of scoring signal quality are contemplated to be within the scope of the present disclosure. The threshold value of 3% is exemplary and other values can be used. In various embodiments, the threshold value can be modified to change the sensitivity, and care can be taken not to set the threshold such that false negative desaturations overwhelm true desaturations.

In various embodiments, the signal quality can be quantified by comparing the quantity of detected features to an expected number of detected features for a given time segment. The length of the time segment can be varied depending on the desired granularity. In various embodiments, signal quality can be expressed as a percentage of expected features for a chosen time segment which are marked features.

Accordingly, various examples of pseudo-actigraphy signals are described, including ECG, polysomnography, and oxygen saturation. These examples are provided for explanation and do not limit the scope of the present disclosure. Other physiological signals can be used as pseudo-actigraphy signals and they are contemplated to be within the scope of the present disclosure. The embodiments described herein for determining signal quality of a physiological signal are exemplary, and other ways of determining signal quality to be a pseudo-actigraphy signal are contemplated to be within the scope of the present disclosure.

Figure 8:
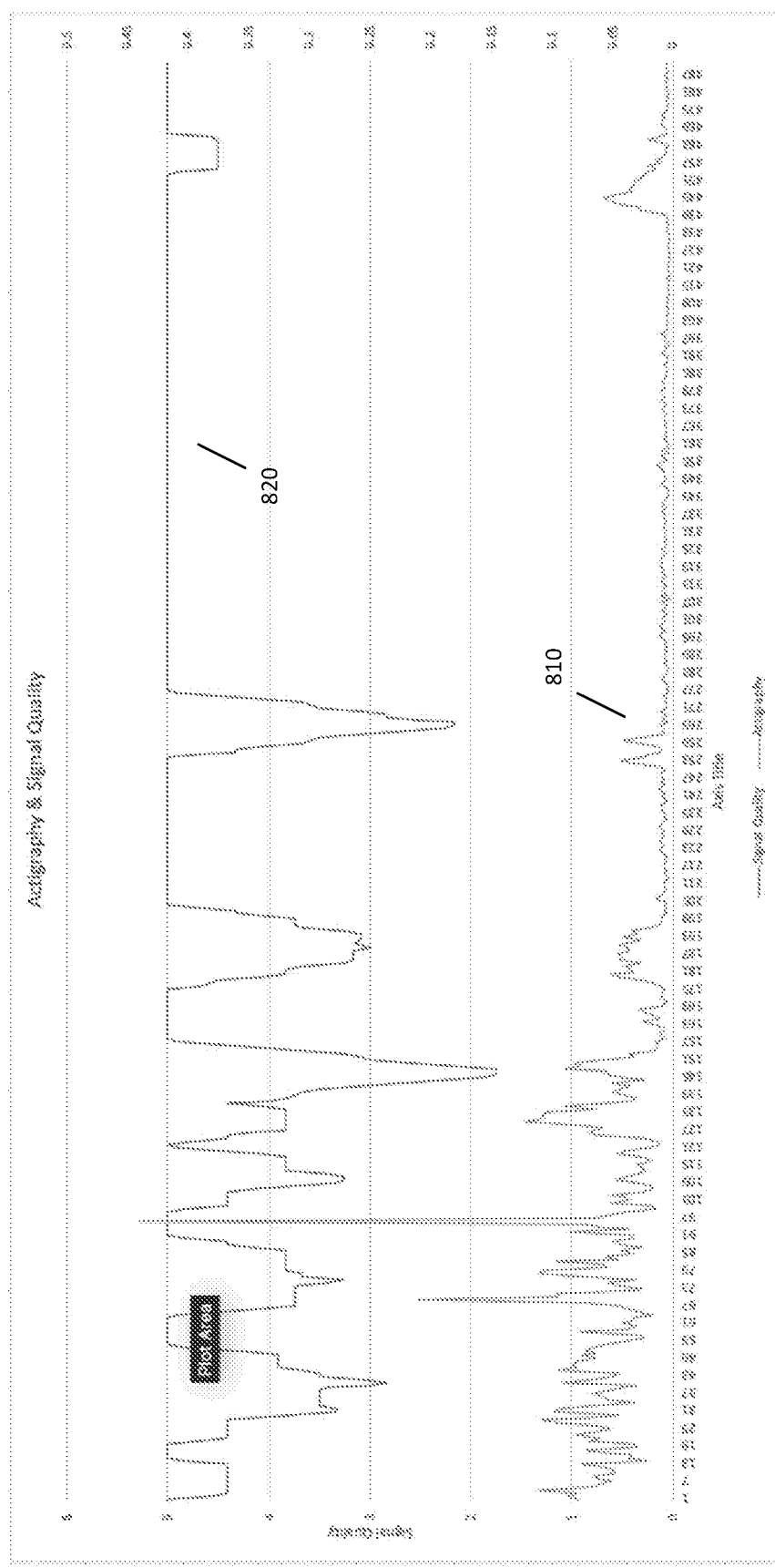
FIG. 8 is a graph of exemplary signal quality measure and actigraphy signal, in accordance with aspects of the present disclosure.

FIG. 8 is a graph of an exemplary actigraphy signal and of an exemplary signal quality of a pseudo-actigraphy signal of a person, with the signal quality score for each time segment on the left y-axis, actigraphy in G/s on the right y-axis, and sample number on the x-axis. As shown in FIG. 8, the actigraphy signal and the signal quality of a pseudo-actigraphy signal are inversely correlated, as the graph shows how the number of high signal quality features decreases with increased actigraphy.

In accordance with aspects of the present disclosure, and with continuing reference to FIG. 7, when oxygen saturation data is available, the disclosed systems and methods can analyze the oxygen saturation data to designate an epoch as REM or WAKE states. In accordance with aspects of the present disclosure, a measurement of blood oxygen saturation ($SO_2$, $SaO_2$, $SpO_2$, etc.) can be analyzed to detect periods of oxygen desaturation events often associated with sleep disordered breathing. The presence of such events during periods of vLFC dominance is indicative of REM sleep. Various techniques and approaches can be used for identifying oxygen desaturation events and/or sleep disordered breathing events, such as the techniques described in International Application Publication No. WO2020061014A1, which is hereby incorporated by reference herein in its entirety. Other techniques and approaches for identifying oxygen desaturation events and/or sleep disordered breathing events using oxygen saturation data are contemplated to be within the scope of the present disclosure.

While each of the aforementioned techniques (e.g., FIGS. 2, 5, 7), can be used independently, they can also be used in combination to increase certainty, accuracy, and/or flexibility based on available signals to aid in designation of REM/WAKE states. These techniques can also aid the diagnosis of sleep disorders specific to the state of REM sleep. For example, "REM Apnea" is considered a subcategory of sleep disordered breathing where apnea/hypopnea events occur during REM sleep. For this purpose, having an oxygen saturation signal may improve the precision of disease classification. Additionally, the complete absence of any period classified as REM through the use of actigraphy, or by analyzing the actigraphy signal during periods where CPC spectral analysis indicates REM, may indicate the presence of REM Behavior Disorder (RBD) where periods of REM are associated with mechanical motion (including sleep-walking).

Figure 9:
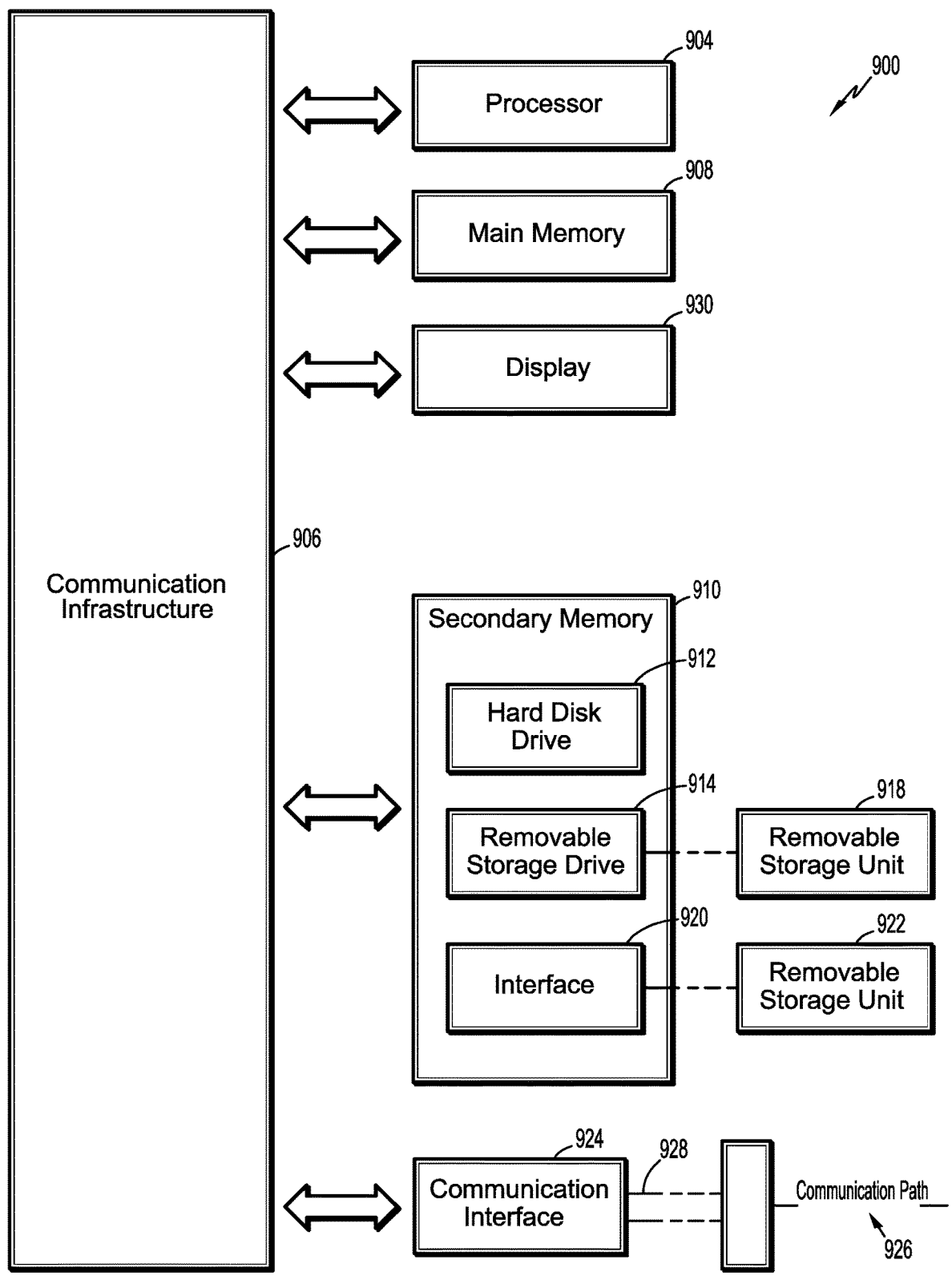
FIG. 9 is a block diagram of an exemplary computing system, in accordance with aspects of the present disclosure.
Figure 10:
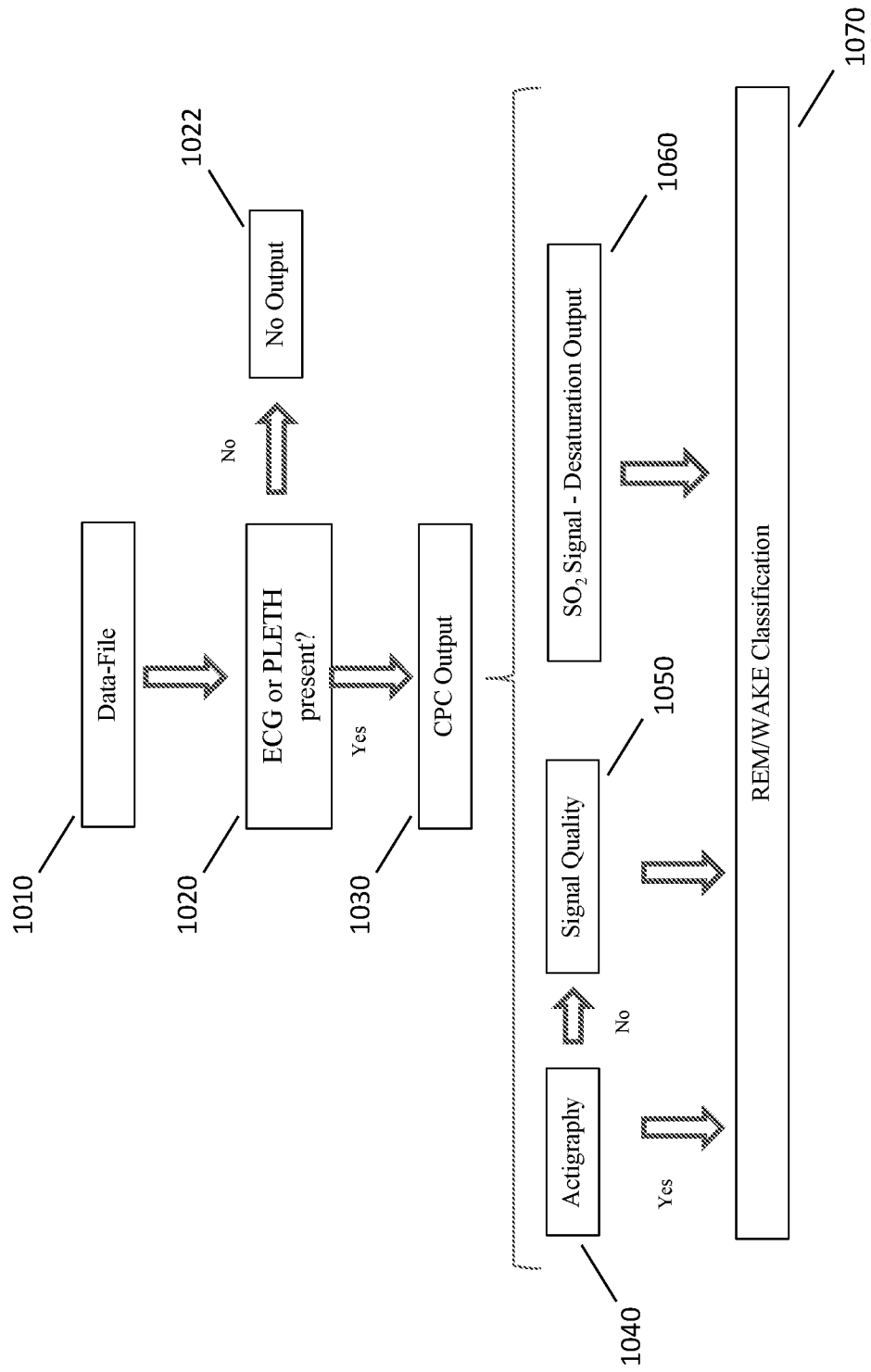
FIG. 10 is a flow diagram of an exemplary operation for designating REM/Wake states based on CPC data and various physiological signals, in accordance with aspects of the present disclosure.

FIG. 10 is a flow chart showing an exemplary operation for deciding which signals to use for REM/WAKE classification. The operation of FIG. 10 can be implemented on a computing system, such as the computing system of FIG. 9, which will be described later. At block 1010, the operation involves reading a data-file to access available signals. At block 1020, the operation involves determining whether ECG and/or plethysmography signals are available. If not, the operation can end at block 1022. If such signals are present, then at block 1030, the operation involves performing CPC processing to generate an array of CPC epochs, and each epoch is classified into one of three CPC states based the dominant frequency band: HFC, LFC, or vLFC. This process can be referred to as "basic labeling". Additionally, each epoch can be classified as having no-eLFC, eLFC$_{BB}$, or eLFC$_{NB}$, and this process can be referred to as "extended labeling". In block 1040, for each epoch that is classified as vLFC, the epoch can be designated as REM state if the extended label has been classified as eLFC$_{NB}$, as described above herein. If a REM/wake state is not designated in block 1030, the operation continues to block 140.

At block 1040, the operation determines if actigraphy data is present. If so, then the operation involves designating an epoch as REM state if motion artifacts are below the predetermined threshold for a sufficient number of samples, as described above in connection with FIG. 5. Otherwise, the epoch is designated as WAKE state. If actigraphy is data is not available, the operation continues to block 1050.

At block 1050, the operation involves using pseudo-actigraphy signals to designate REM/WAKE state, as described in connection with FIG. 7. For example, if the sum of excess and missed N-N intervals detected is below the predetermined threshold, and the oxygen saturation signal quality (if present) has no artifact, the epoch can be designated as REM state.

At block 1060, the operation involves determining whether oxygen saturation signal is present. If so, the operation determines whether there are desaturation events and no artifacts. If there are desaturation events and no artifacts, the operation can designate the epoch as REM state.

Accordingly, an array of sleep stage classifications 1070 is generated based on the above operations. The operations described above are exemplary and variations are contemplated to be within the scope of the disclosure. For example, in various embodiments, presence of desaturation events as determined by block 1060 could override the decisions of blocks 1040 and/or 1050, or could cause blocks 1040 and/or 1050 to designate the epoch as "unknown" state.

The operation of FIG. 10 is exemplary and other ways of using combinations of physiological data with CPC data to determine REM/Wake states are contemplated to be within the scope of the present disclosure.

The aspects and embodiments of the present disclosure can be implemented in one or more computing systems capable of carrying out the functionality described herein. Referring to FIG. 9, an example of a computing system 900 for implementing the present disclosure is shown. Various embodiments of the disclosure described herein can be implemented by the computing system 900. However, it will be apparent to one skilled in the relevant art(s) how to implement the disclosure using other computer systems and/or computer architectures.

The computing system 900 includes one or more processors, such as processor 904. The processor 904 is connected to a communication infrastructure 906 (e.g., a communications bus, crossover bar, or network).

Computing system 900 can include a display 930 that receives graphics, text, and other data from the communication infrastructure 906 (or from a frame buffer not shown) for display. In various embodiments, the display 930 can present various measurements and metrics described herein, including the CPC data, actigraphy data, oxygen saturation data, ECG data, and/or plethysmography data, among others. In various embodiments, the display 930 can present graphical and numerical presentations. The presentations and reports can include some or all of the various metrics disclosed above herein.

Computing system 900 also includes a main memory 908, preferably random access memory (RAM), and can also include a secondary memory 910. The secondary memory 910 can include, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a known manner. Removable storage unit 918, represents a floppy disk, magnetic tape, optical disk, etc. which is read by and written to removable storage drive 914. As will be appreciated, the removable storage 918 includes a computer usable storage medium having stored therein computer software (e.g., programs or other instructions) and/or data.

In various embodiments, secondary memory 910 can include other similar devices for allowing computer software and/or data to be loaded into computing system 900. Such devices can include, for example, a removable storage 922 and an interface 920. Examples of such can include a program cartridge and cartridge interface (such as that found in legacy devices), a removable memory chip (such as an EPROM, or PROM) and associated socket, and other removable storage devices 922 and interfaces 920 which allow software and data to be transferred from the removable storage device 922 to computing system 900.

Computing system 900 can also include a communications interface 924. Communications interface 924 allows software and data to be transferred between computing system 900 and external devices. Examples of communications interface 924 can include a modem, a network interface (such as an Ethernet or WiFi card), a communications port, a PCMCIA or SD or other slot and card, among other components. Software and data transferred via communications interface 924 are in the form of signals 928 which can be electronic, electromagnetic, optical, or other signals capable of being received by communications interface 924. These signals 928 are provided to communications interface 924 via a communications path (i.e., channel) 926. Communications path 926 carries signals 928 and can be implemented using wire or cable, fiber optics, a phone line, a cellular phone link, an RF link, free-space optics, and/or other communications channels.

As used herein, the terms "computer program medium" and "computer usable medium" are used to generally refer to media such as removable storage 918, removable storage 922, a hard disk installed in hard disk drive 912, and signals 928. These computer program products are devices for providing software to computing system 900. The present disclosure includes such computer program products.

Computer programs (also called computer control logic or computer readable program code) are stored in main memory 908 and/or secondary memory 910. Computer programs can also be received via communications interface 924. Such computer programs, when executed, enable the computing system 900 to implement the present disclosure as discussed herein. In particular, the computer programs, when executed, enable the processor 904 to implement the processes and operations of the present disclosure, such as the various operations of FIGS. 2, 5, and/or 7, for example, described above. Accordingly, such computer programs represent controllers of the computing system 900.

In an embodiment where the disclosure is implemented using software, the software can be stored in a computer program product and loaded into computing system 900 using removable storage drive 914, hard drive 912, interface 920, or communications interface 924. The control logic (software), when executed by the processor 904, causes the processor 904 to perform the functions of the disclosure as described herein. Accordingly, the technology of the present disclosure may be provided as software as a medical device (SaMD) or as a non-medical software. In various embodiments, the software may include cloud-based applications.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a representative basis for teaching one skilled in the art to variously employ the present disclosure in virtually any appropriately detailed structure.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, a program, where the programming language could exist in more than one state (such as source, compiled, object, or linked) is a reference to any and all such states.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above are also intended to be within the scope of the disclosure.

What is claimed is:

1. A computer-implemented method comprising:
computing cardiopulmonary coupling data spanning a sleep period for a person;
classifying an epoch in the sleep period as a very-low frequency coupling (vLFC) epoch based on the cardiopulmonary coupling data;
accessing pseudo-actigraphy data for the person corresponding to the vLFC epoch, wherein the pseudo-actigraphy data is based on physiological measurements of the person and is not based on actigraphy measurements, and wherein the physiological measurements, on which the pseudo-actigraphy data is based, are separate and different from the cardiopulmonary coupling data;
determining, based on the pseudo-actigraphy data corresponding to the vLFC epoch, between a REM epoch and a wake epoch to distinguish between a REM epoch and a wake epoch for the vLFC epoch; and
designating the vLFC epoch as a REM epoch or as a wake epoch based on a result of the determining.

2. The computer-implemented method of claim 1, further comprising generating the pseudo-actigraphy data corresponding to the vLFC epoch based on signal quality of the physiological measurements.

3. The computer-implemented method of claim 2, wherein generating the pseudo-actigraphy data includes quantifying the signal quality of the physiological measurements.

4. The computer-implemented method of claim 3, wherein the physiological measurements include at least one of ECG measurements or plethysmography measurements of the person.

5. The computer-implemented method of claim 4, wherein quantifying the signal quality of the physiological measurements includes:
processing the physiological measurements to detect peaks during the vLFC epoch;
generating data indicating higher signal quality when a count of the detected peaks is below a predetermined threshold and when shapes of the detected peaks match expected peak shapes; and
generating data indicating lower signal quality when the count of the detected peaks is greater than the predetermined threshold and when the shapes of the detected peaks differ from the expected peak shapes.

6. The computer-implemented method of claim 3, wherein the physiological measurements include oxygen saturation measurements.

7. A system comprising:
one or more processors; and
at least one memory storing instructions which, when executed by the one or more processors, cause the system to:
compute cardiopulmonary coupling data spanning a sleep period for a person;
classify an epoch in the sleep period as a very-low frequency coupling (vLFC) epoch based on the cardiopulmonary coupling data;
access pseudo-actigraphy data for the person corresponding to the vLFC epoch, wherein the pseudo-actigraphy data is based on physiological measurements of the person and is not based on actigraphy measurements, and wherein the physiological measurements, on which the pseudo-actigraphy data is based, are separate and different from the cardiopulmonary coupling data;
determine, based on the pseudo-actigraphy data corresponding to the vLFC epoch, between a REM epoch and a wake epoch to distinguish between a REM epoch and a wake epoch for the vLFC epoch; and
designate the vLFC epoch as a REM epoch or as a wake epoch based on a result of the determining.

8. The system of claim 7, wherein the instructions, when executed by the one or more processors, further cause the system to generate the pseudo-actigraphy data corresponding to the vLFC epoch based on signal quality of the physiological measurements.

9. The system of claim 8, wherein in generating the pseudo-actigraphy data, the instructions, when executed by the one or more processors, cause the system to quantify the signal quality of the physiological measurements.

10. The system of claim 9, wherein the physiological measurements include at least one of ECG measurements or plethysmography measurements of the person.

11. The system of claim 10, wherein in quantifying the signal quality of the physiological measurements, the instructions, when executed by the one or more processors, cause the system to:
process the physiological measurements to detect peaks during the vLFC epoch;
generate data indicating higher signal quality when a count of the detected peaks is below a predetermined threshold and when shapes of the detected peaks match expected peak shapes; and
generate data indicating lower signal quality when the count of the detected peaks is greater than the predetermined threshold and when the shapes of the detected peaks differ from the expected peak shapes.

12. The system of claim 9, wherein the physiological measurements include oxygen saturation measurements.

* * * * *